United States Patent [19]

Ngo et al.

[11] Patent Number: 5,230,247

[45] Date of Patent: Jul. 27, 1993

[54] METHOD OF ASSESSING FAULTS IN METAL TUBES HAVING INTERNAL HELICAL RIBS

[75] Inventors: Phu-Ann Ngo; Olivier Tailleux, both of Aulnoye Ayneries; Hervé Wiart, Bourham, all of France

[73] Assignee: Valtubes, Boulogne-Billancourt, France

[21] Appl. No.: 705,584

[22] Filed: May 24, 1991

[30] Foreign Application Priority Data

May 28, 1990 [FR] France ................... 90 06825

[51] Int. Cl.$^5$ ................... G01N 29/24; G01N 29/10
[52] U.S. Cl. ................... 73/598; 73/602; 73/900; 73/622
[58] Field of Search ............ 73/602, 598, 622, 629, 73/623, 900

[56] References Cited

U.S. PATENT DOCUMENTS

| | | | |
|---|---|---|---|
| 4,016,750 | 4/1977 | Green | 73/629 |
| 4,056,971 | 11/1977 | van Valkenburg et al. | 73/629 |
| 4,098,130 | 7/1978 | Coffey et al. | 73/602 |
| 4,145,741 | 3/1979 | Nappin | 73/602 |
| 4,487,072 | 12/1984 | Livingston | 73/622 |
| 4,599,900 | 7/1986 | Friedman | 73/622 |

FOREIGN PATENT DOCUMENTS

| | | |
|---|---|---|
| 0102176 | 3/1984 | European Pat. Off. . |
| 0294255 | 12/1988 | European Pat. Off. . |
| 2195351 | 3/1974 | France . |
| 2361649 | 3/1978 | France . |

OTHER PUBLICATIONS

Patent Abstracts of Japan, vol. 8, No. 1 (P-246) [1438], Jan. 6, 1984; & JP-A-58 165 073 (Mitsubishi) Sep. 30, 1983.

Primary Examiner—Hezron E. Williams
Assistant Examiner—Rose M. Finley
Attorney, Agent, or Firm—Oblon, Spivak, McClelland, Maier & Neustadt

[57] ABSTRACT

A method for the detection and evaluation of faults existing on the walls of metal tubes having internal helical ribs includes for each fault signal received by an ultrasonic emitter-receiver ER, the length of the to-and-fro travel completed by the ultrasonic beam corresponding to the signal is determined and after the amplitude of the signal has been compared with a specific threshold, a correction is applied to one of the terms of the comparison, taking into account the length of travel completed by the signal.

4 Claims, 2 Drawing Sheets

METHOD OF ASSESSING FAULTS IN METAL TUBES HAVING INTERNAL HELICAL RIBS

BACKGROUND OF THE INVENTION

The method which is the object of the invention relates to the detection, location and assessment of faults existing on the walls of metal tubes having internal helical ribs.

In particular, this method relates to faults present in tubes used mainly for the production of heat exchangers for fuelled power stations. According to their conditions of use, such tubes may be made from non-alloyed, stainless or refractory steels or from other metals or alloys.

In known manner, systematic ultrasonic inspections are carried out on these tubes to make sure that any longitudinal or transverse cracks formed on the outer or inner walls do not attain a depth which is likely to lead to their subsequent breakdown.

At the present time, the existence of such cracks on such tubes are detected by means of ultrasonic waves. According to the state of the art, FIG. 1 shows how faults are looked for on the outer wall of a metal tube 1 which has no ribs. An ultrasonic emitter-receiver transducer emits an ultrasonic beam having an inclined axis at an angle "i" in relation to the radius of the tube of axis X1 in the sectional plane of the drawing. The tube is propelled in relation to the transducer ER and performs a relative movement of rotation about its axis while sliding along this axis. It can be seen that an external longitudinal crack R is detected by an ultrasonic beam emanating from the transducer ER which travels the path ABC in the wall of the tube with total reflection at B, a part of the beam being returned to the transducer by the fault R along the path CBA.

Thanks to the known electronic means, the amplitude of the signal corresponding to the fault R may be determined and compared With the amplitude of a standard fault which is stored in the memory. It is then possible to eliminate those tubes in which the cracks, detected by ultrasound, provide signals of an amplitude equal to or greater than a threshold corresponding to the amplitude of the signal given by the standard fault.

Tests carried out in order to apply the same method of ultrasonic detection and inspection for external or internal cracks and fissures on internally ribbed tubes have shown that the existence of ribs resulted in quite substantial fluctuations in the amplitude of the fault signals received by the transducer. The outcome is that it was not possible reliably to compare this amplitude with a specific threshold. It was then necessary to adopt quite a wide safety margin, entailing the risk of rejecting tubes of good quality or, on the other hand, to reduce the safety margin and take the risk of accepting tubes which do not comply with the standards or specifications.

The possibility was sought of perfecting a method of using ultrasonic waves to detect and check for faults in metal tubes having internal ribs and which make it possible to take into account fluctuations in amplitude observed during the course of detection of one and the same fault so that this fault may be compared with a standard by automatically employing electronic signal processing means.

SUMMARY OF THE INVENTION

The method which is the object of the invention makes it possible to resolve this problem. This method makes it possible to detect and assess faults present on the external or internal walls of a metal tube having an outer wall of revolution comprising internal helical ribs whether the faults present are longitudinal or transversal. In this method, ultrasonic detection means are employed which comprise at least one emitter-receiver which emits an ultra-sonic beam which penetrates the wall of the tube; the beam is orientated in a plane at right-angles to the axis of travel of the tube with an angle of incidence which makes it possible to obtain a high level of detection sensitivity. Any signal corresponding to the interception of a fraction of a fault is received by the receiver and processed by automatic electronic means in order to compare its amplitude with an amplitude threshold corresponding to a standard fault. According to the invention, the automatic electronic processing means first determines the length of to-and-fro travel completed by the ultrasonic beam corresponding to each fault signal within the wall of the tube and provide a correction to the amplitude of the signal or to that of the threshold prior to comparison; this correction depends on the difference which exists between the length of travel actually completed by the signal and that of the path of the signal for which the amplitude of the threshold has been determined; if the difference between the two lengths of travel is nil, then this correction is likewise nil. The comparison is then performed in known manner.

The tube is propelled in relation to the emitter-receiver to perform a relative movement of rotation about its axis and also a movement whereby it advances along this axis.

According to a first particular embodiment of the method according to the invention, the automatic electronic means of processing signals determine for each signal received the travel which the signal has effectively completed from among the possible paths, by means of a measurement of the length of this travel and they perform a correction of amplitude corresponding to the travel completed in order to make this corrected signal amplitude correspond to that which it would have been had it travelled the distance for which the amplitude of the comparison threshold was intended.

According to a second particular embodiment of the method according to the invention, the electronic automatic signal processing means, after having determined for each signal received the distance Which it has actually travelled, by measuring the length of the distance, covered, carry out a comparison of the amplitude of this corrected signal with a threshold the amplitude of which has been adjusted to take into account the length of the distance actually travelled by the signal.

Advantageously, when comparison thresholds are used of which the amplitude is adjusted for each distance likely to be travelled by each signal this set of threshold amplitude values is stored in a memory so that they can be used in the processing of signals.

A vast number of alternative forms or modifications may be applied to the method which is the object of the invention without thereby departing from the scope thereof.

BRIEF DESCRIPTION OF THE DRAWINGS

In a non-limitative manner the following example of a particular form of embodiment of the method according to the invention is described hereinafter with reference to the accompanying drawings, in which.

DETAILED DESCRIPTION OF THE PREFERRED EMBODIMENTS

Figure 1:
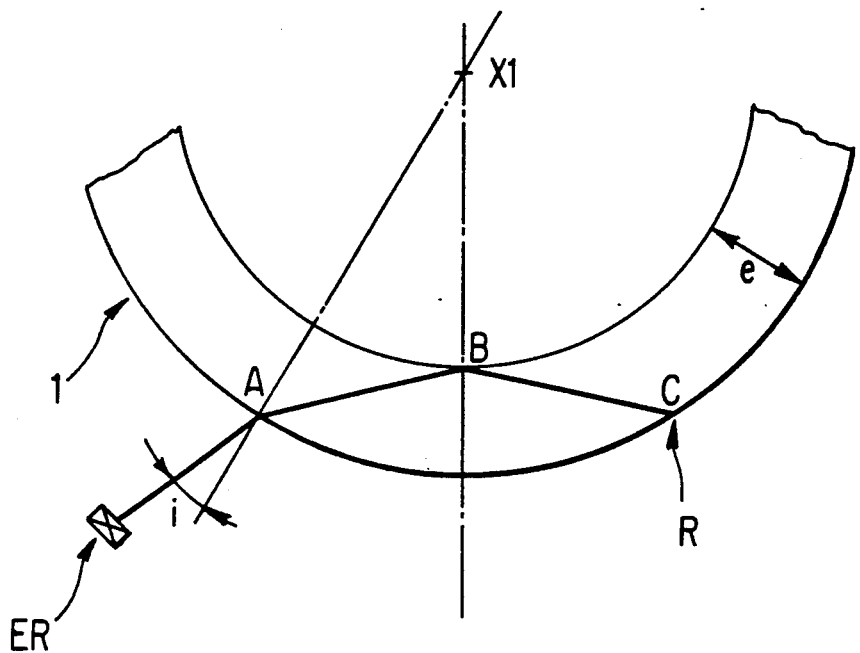
FIG. 1 represents a cross-section through a tube of revolution which has no ribs, showing the conditions of detection of cracks on the inner or outer walls of this tube using ultrasonic waves.

As indicated earlier when disclosing the state of the art, FIG. 1 shows the conditions of use of an ultrasonic emitter-receiver transducer ER for the detection of faults such as longitudinal cracks and fissures in the external or internal wall of a metal tube.

In the case of FIG. 1, it is noted that assuming the position of the sensor ER to be fixed, the tube 1 of thickness "e" rotating about its axis Xl at a slow speed while sliding along this axis also at a slow speed, only one single path ABC inside the wall of the tube 1 is possible for the ultra-sonic beam to reach a longitudinal crack such as R. In known manner, a fraction of the beam is intercepted by this crack and regains the transducer ER after travelling a return distance which is identical to the outward path. The speed of rotation of the tube is sufficiently low that everything takes place as if the tube were immobile. It will be appreciated that the detection of fissures on the internal wall of the tube 1 may be carried out directly by means of an ultrasonic beam which performs the to-and-fro travel AB.

Figure 2:
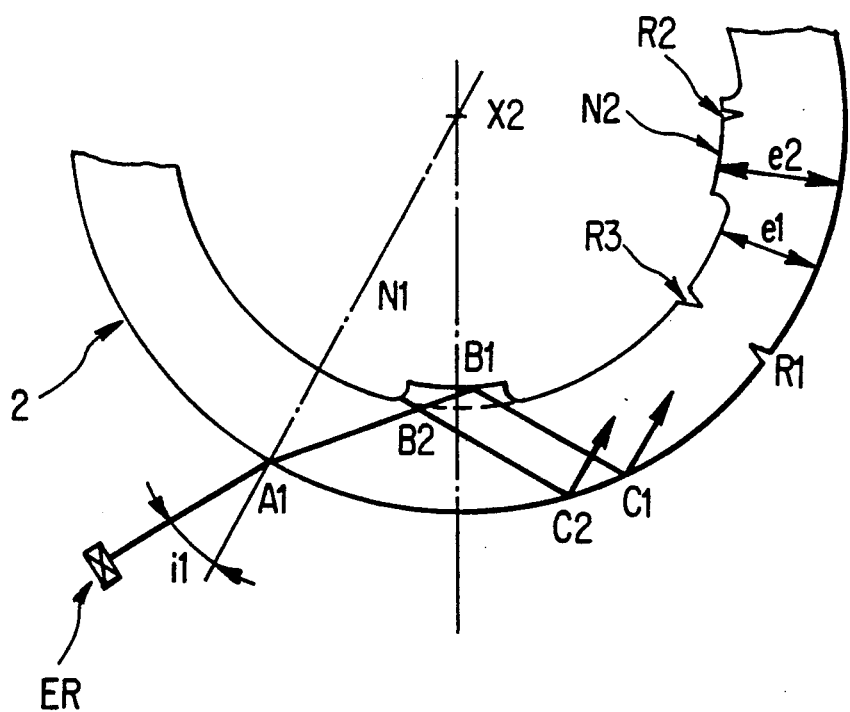
FIG. 2 represents a cross-section of a tube of revolution ribbed on the internal wall and showing the various possible distances which may be travelled by the ultrasonic beam due to the presence of the ribs.

In the case of FIG. 2, the tube 2 comprises ribs such as N1, N2. The thickness "e2" at right-angles to the ribs is markedly greater than the thickness "e1" between two ribs. It can be seen that detection of an external longitudinal crack R1 may be carried out either by following the path A1 B1 C1, where the ultrasonic beam is reflected at the apex of the rib N1, or by following the path A1 B2 C2 which is markedly shorter where there is a reflection on the interior wall between two ribs. Indeed, it is worth while noting that if the crack R1 is longitudinal and therefore parallel with the generatrices, it will assume position C1 or C2 as the tube slides slide along its axis X2, the ribs such as N1, N2 being helical. For the same reasons, the longitudinal cracks R2, R3, formed on the internal wall of the tube, may be found between the ribs or on one of them or indeed, if they are sufficiently long, it may straddle ribs.

In accordance with the method according to the invention, the ultrasonic signals corresponding to faults such as R1, R2, R3 are processed by automatic electronic means not shown but to which is connected the transducer ER in order to determine, in a first phase for each signal received and in a conventional manner, the length of to-and-fro travel completed by the ultrasonic beam. A comparison of these lengths of travel with the actual lengths of travel possible for the four to-and-fro journeys A1 B1 C1, A1 B2 C2, A1 B1 and A1 B2, indicated in FIG. 2, makes it possible to classify these signals so that each is in a category corresponding to one of these distances travelled. It is then possible to compare each signal with, a reference threshold corresponding to a standard fault by correcting the amplitude of the signal or the height of the threshold in order to take into account the length of travel actually completed by the ultrasonic beam associated with this corrected signal.

Such a comparison then makes it possible, independently of the path travelled by the ultrasonic beam generating the signal, to establish whether the detected fault is or is not greater than the standard fault to which the comparison threshold corresponds.

Figure 3:
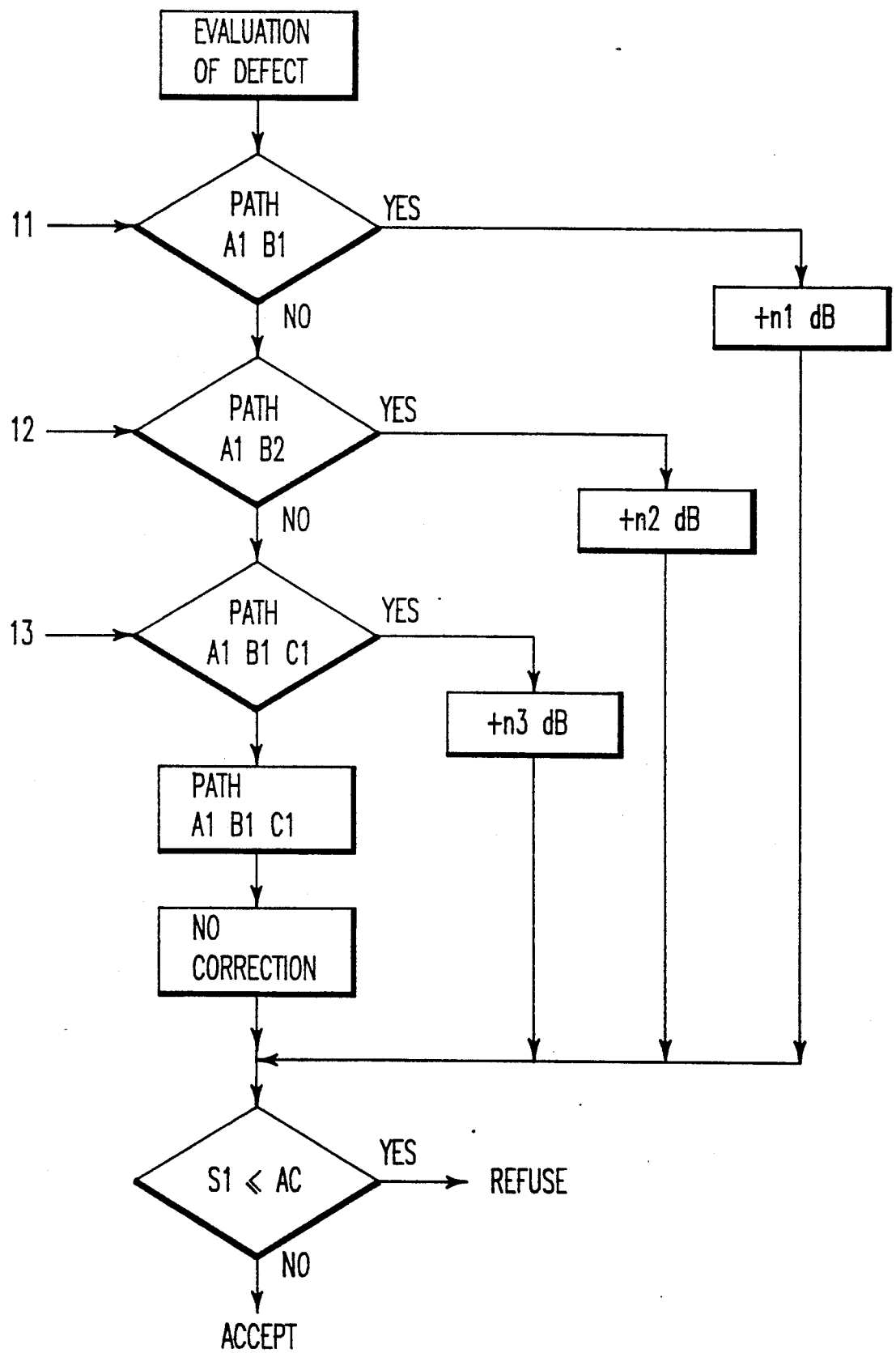
FIG. 3 is a diagram showing an embodiment of the automatic method according to the invention for evaluating faults detected by ultrasound.

FIG. 3 is a diagram showing a flow chart of the automatic operations for assessing faults using the method according to the invention and employing electronic processing means which are known per se. It can be seen that the length of travel of the signal is compared at 11 with the travel distance A1 B1. If there is equality, n1 dB is added to the amplitude of the signal prior to comparison of this corrected amplitude AC with the amplitude of the threshold S1 of acceptance or rejection. If the length travelled by the signal is not A1 B1, there is again a comparison at 12 with A1 B2 and possibly at 13 with A1 B1 C1. The corrective additions n2 dB and n3 dB are respectively added.

If the travel of the signal is A1 B2 C2 on condition that the threshold amplitude is determined for a standard fault of which the amplitude of the signal is itself adjusted to correspond to such a travel, no addition need be made.

The various corrections of amplitude of ultrasonic signals such as n1 dB, n2 dB, n3 dB are preferably determined by comparison of the amplitudes of the ultrasonic signals obtained according to the various possible distances travelled by the ultrasonic beam through the wall of the tube.

By thus applying the method according to the invention, it is possible reliably to compare the faults in tubes with a threshold and therefore to reject the tubes in which the faults exceed the threshold, without any risk of rejecting acceptable tubes.

Reciprocally, there is no risk of accepting tubes which exhibit cracks of an amplitude which exceeds that of the standard cracks.

We claim:

1. A method of assessing faults on an external of internal wall of a metal tube having an external wall of revolution and helical ribs on the internal wall, comprising the steps of:

producing a helical movement of the metal tube relative to at least one ultrasonic detector;

emitting an ultrasonic beam such that the beam penetrates one wall of the metal tube and is reflected to the ultrasonic detector, wherein a portion of the beam is reflected by a fault in the tube so that the ultrasonic detector outputs a signal indicative of the reflected beam received by the ultrasonic detector;

determining a length of travel of the beam in the tube;

selectively correcting one of a threshold value signal and the detector output signal as a function of the determined length of travel to produce a corrected signal;

comparing the corrected signal with the other of the threshold value signal and the detector output signal; and assessing faults in the tube on a basis of the comparing step.

2. The method of claim 1 wherein said step of selectively correcting comprises applying an amplitude correction value to the selected signal.

3. The method of claim 2 including the step of rotating and axially moving the tube during said emitting step to produce the helical movement.

4. The method of claim 1 wherein the selectively corrected signal is the threshold value signal, said step of selectively correcting comprises applying an amplitude correction to the threshold value signal corresponding to a standard fault.

* * * * *

UNITED STATES PATENT AND TRADEMARK OFFICE
CERTIFICATE OF CORRECTION

PATENT NO.   :  5,230,247
DATED        :  July 27, 1993
INVENTOR(S)  :  Phu-Ann Ngo et al.

It is certified that error appears in the above-indentified patent and that said Letters Patent is hereby corrected as shown below:

On the title page, Item [75],

The third inventor's city is spelled incorrectly, should read:

--Bourlon--

Signed and Sealed this

Third Day of May, 1994

Attest:

BRUCE LEHMAN

Attesting Officer

Commissioner of Patents and Trademarks